United States Patent [19]

Ogiu et al.

[11] Patent Number: 4,667,655
[45] Date of Patent: May 26, 1987

[54] ENDOSCOPE APPARATUS

[75] Inventors: Hisao Ogiu; Koji Yamaya, both of Tokyo, Japan

[73] Assignee: Olympus Optical Co., Ltd., Tokyo, Japan

[21] Appl. No.: 819,359

[22] Filed: Jan. 16, 1986

[30] Foreign Application Priority Data

Jan. 21, 1985 [JP] Japan ............................ 60-8742
Oct. 2, 1985 [JP] Japan ...................... 60-150955[U]

[51] Int. Cl.$^4$ .................................................. A61B 1/06
[52] U.S. Cl. ............................................................ 128/6
[58] Field of Search ....................................... 128/4–8,
128/15, 16; 73/151; 137/625.18; 433/84, 85, 100

[56] References Cited

U.S. PATENT DOCUMENTS

| 4,261,343 | 4/1981 | Ouchi et al. | 128/4 |
| 4,281,646 | 8/1981 | Kinoshita | 128/6 |
| 4,311,134 | 1/1982 | Mitsui et al. | 128/6 |
| 4,325,362 | 4/1982 | Ouchi et al. | 128/4 |
| 4,509,507 | 4/1985 | Yabe | 128/4 |
| 4,550,716 | 11/1985 | Kinoshita | 128/6 |

Primary Examiner—Kyle L. Howell
Assistant Examiner—Max F. Hindenburg

[57] ABSTRACT

An endoscope includes a view window and a washing nozzle which are provided at the distal end of an insertion section extending from an operation section. Universal cord extends from the operation section, and a connector is fitted to the extended end of the cord. Air and liquid supply channels extend through the endoscope, each having one end connected to the nozzle and the other end opening to the connector. A selector valve is provided at the operation section and connected to the middle portions of the supply channels. An air-liquid supply device is connected to the connector. The device includes an air pump for supplying compressed air to the air supply channel, tank stored with water and a liquid pump for pressurizing the water in the tank to supply the water to the liquid supply channel.

7 Claims, 10 Drawing Figures

ENDOSCOPE APPARATUS

BACKGROUND OF THE INVENTION

The present invention relates to an endoscope apparatus, and more specifically to an endoscope apparatus in which a mixture of water and air is sprayed onto a view window through a nozzle provided at the distal end of an insertion section.

In general, an endoscope comprises an operation section and an insertion section extending therefrom. A view window and a washing nozzle are arranged at the distal end of the insertion section. A mixture of air and water is sprayed onto the window to wash it.

The washing nozzle is connected with one end of an air supply channel and a liquid supply channel extending inside the insertion section. Air and water are compressed by a single pump, supplied through the air and liquid supply channels, respectively, and sprayed from the nozzle. If the flow resistance of the liquid supply channel is increased from various causes, however, the water flowing through the liquid supply channel is reduced, while the air fed into the air feed channel is increased. In this case, excessive air would be introduced into the patient to cause pain to him or her.

SUMMARY OF THE INVENTION

The present invention is contrived in consideration of these circumstances, and is intended to provide an endoscope apparatus capable of supplying enough water to a nozzle despite an increase in flow resistance of a liquid supply channel.

In order to achieve the above object, an endoscope apparatus according to the present invention comprises an air pump for feeding compressed air into an air supply channel, a liquid pump for feeding compressed water into a liquid supply channel, and selector means provided at an operation section. The selector means includes a cylinder communicating with the middle portions of the air and liquid supply channels, and a piston inserted in the cylinder and movable between a first position where it prevents air and water from flowing to the nozzle and a second position where it permits the flow of air and water to the nozzle.

In this endoscope apparatus, air and water are fed to a nozzle after they are compressed by separate pumps, so that the liquid supply channel can be supplied with enough water despite an increase in the flow resistance of the liquid supply channel. Thus, excessive air supply can be prevented.

BRIEF DESCRIPTION OF THE DRAWINGS

FIGS. 1 to 7 show an endoscope apparatus according to an embodiment of the present invention, in which FIGS. 8 to 10 show a modified example of the liquid feed plug, in which

DETAILED DESCRIPTION OF THE PREFERRED EMBODIMENTS

An endoscope apparatus according to an embodiment of the present invention will now be described in detail with reference to the accompanying drawings.

Figure 1:
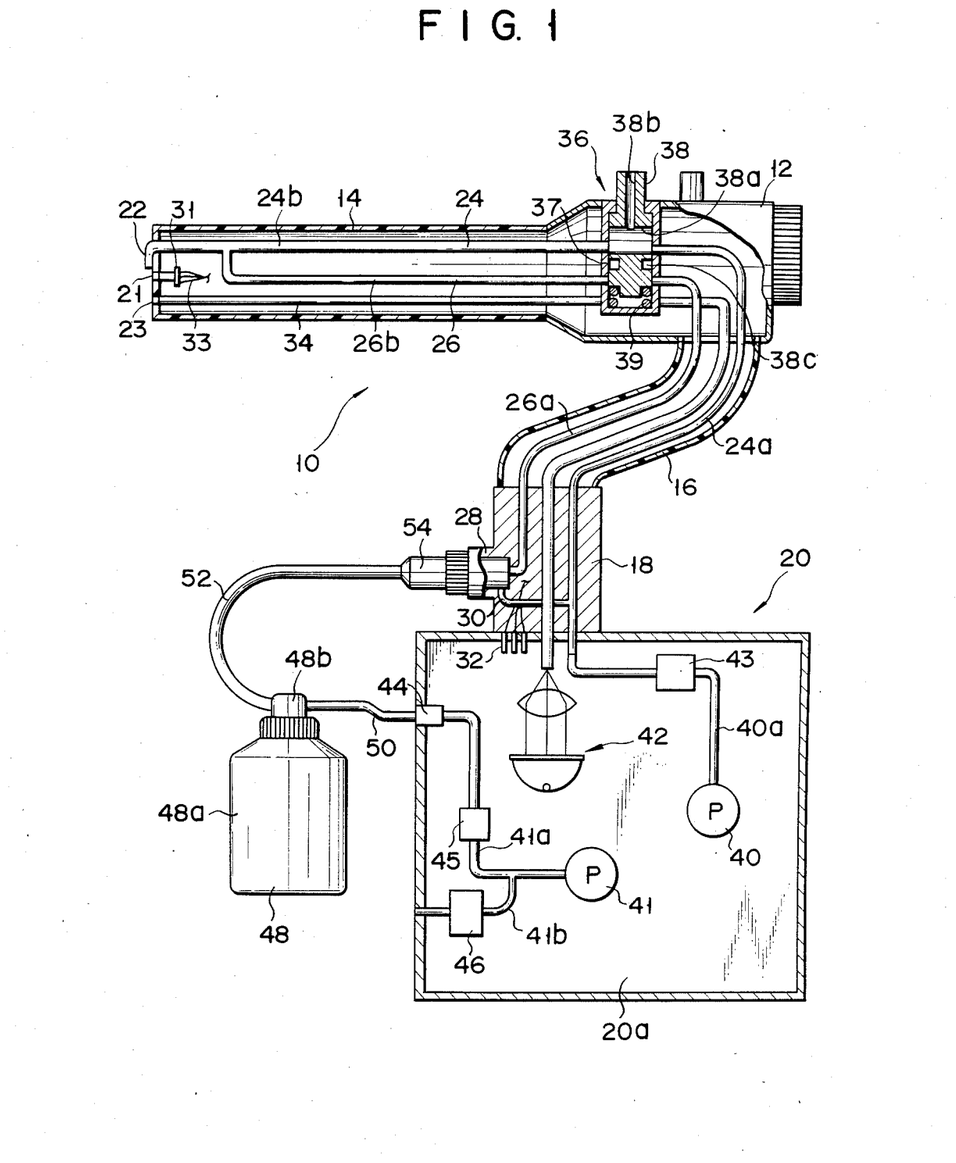
FIG. 1 is a sectional view showing an outline of the apparatus.

As shown in FIG. 1, the endoscope apparatus is provided with endoscope 10. Endoscope 10 includes operation section 12, insertion section 14, and universal cord 16, sections 14 and 16 both extending from section 12. Connector 18 is fixed to the extended end of cord 16, and connected to air-liquid supply device 20.

Insertion section 14 is provided, at its distal end, with view window 21, washing nozzle 22 directed toward window 21, and illumination window 23. Air supply channel 24 and liquid supply channel 26 extend through insertion section 14, operation section 12, and universal cord 16. One end of channel 24 is connected to nozzle 22, while its other end projects outward from connector 18. One end of liquid supply channel 26 is connected to that portion of air supply channel 24 which is near nozzle 22. The other end of channel 26 opens to liquid feed mouthpiece 28 which is formed on connector 18. The other end portion of air supply channel 24 communicates with mouthpiece 28 by means of bypass passage 30 which is formed in connector 18.

Inside insertion section 14, solid-state image sensor 31 is opposed to view window 21. Element 31 is connected by lead wires 33 to connecting terminal 32 formed at the other end of connector 18. One end of light guide 34 is optically connected to illumination window 23. Guide 34 extends through insertion section 14, operating section 12, and universal cord 16 and projects from the connector 18.

Operation section 12 is provided with selector valve 36. Valve 36 includes cylinder 37 disposed in section 12 and communicating with the middle portions of channels 24 and 26, and piston 38 slidably inserted in cylinder 37. Piston 38 is urged to a first position, as shown in FIG. 1, by spring 39 disposed in cylinder 37. Piston 38 is formed with diametrical through hole 38a and leak hole 38b which opens, at one end, to the outside of operating section 12, and at the other end, into hole 38a. Annular groove 38c s formed in the outer peripheral surface of piston 38. Hole 38a as a diameter much greater than air supply channel 24. When piston 38 is in the first position, upper- and lower-course portions 24a and 24b of channel 24 communicate with each other through hole 38a. Upper- and lower-course portions 26a and 26b of liquid supply channel 26 are disconnected by piston 38. When piston 38 is forced into a second position against the urging force of spring 39, portions 24a and 24b of air supply channel 24 are kept connected by hole 38a, and portions 26a and 26b of liquid supply channel 26 are connected by annular groove 38c.

Air-liquid supply device 20 is provided with housing 20a. Air pump 40, liquid pump 41, and light source 42 are arranged in housing 20a. Pump 40 is connected to the other end of air supply channel 24 by air feed pipe 40a, and first throttle valve 43 is attached to the middle portion of pipe 40a. A light beam emitted from light source 42 enters light guide 34 at the other end thereof, passes through guide 34, and is radiated from illumination window 23. Tank-connecting mouthpiece 44 is formed on a lateral face of housing 20a. Liquid pump 41 is connected to mouthpiece 44 by liquid feed pipe 41a. Second throttle valve 45 is attached to the middle portion of pipe 41a. Release pipe 41b opening to the outside of housing 20a is connected to that portion of liquid feed pipe 41a which is located between pump 41 and valve 45. Solenoid valve 46 is attached to the middle portion of pipe 41b. Also arranged in housing 20a is a video processing circuit (not shown) which is connected to connecting terminal 32.

Figure 2:
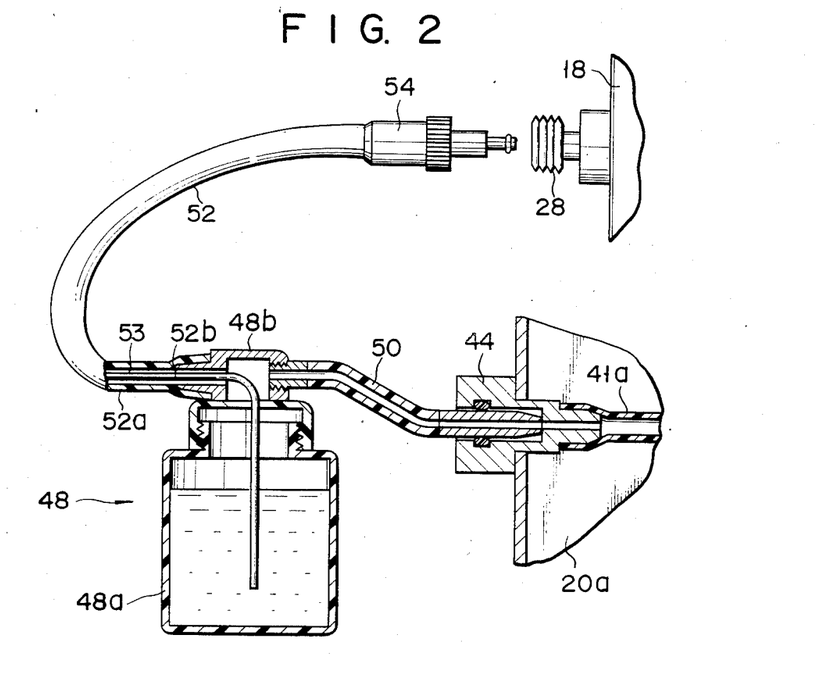
FIG. 2 is a sectional view showing a water tank and its surroundings.

As shown in FIGS. 1 and 2, water tank 48 is provided outside housing 20a. Tank 48 includes open-topped tank body 48a and connecting cap 48b removably attached to a top opening of body 48a. Water is stored in body 48a. Connecting tube 50 extends from cap 48b, communicating with the inside of tank 48. The extreme end of tube 50 is detachably connected to connecting mouthpiece 44 of housing 20a. Liquid feed tube 52 also extends from cap 48b Tube 52 includes outer tube 52a communicating with the inside of tank 48, and pumping tube 52b extending through outer tube 52a. One end of tube 52b extends close to the bottom of tank 48. Air passage 53 is defined between the inner surface of outer tube 52a and pumping tube 52b. Liquid feed plug 54 is attached to the extended end of liquid feed tube 52. Plug 54 is detachably connected to liquid feed mouthpiece 28 of endoscope 10.

Figure 3:
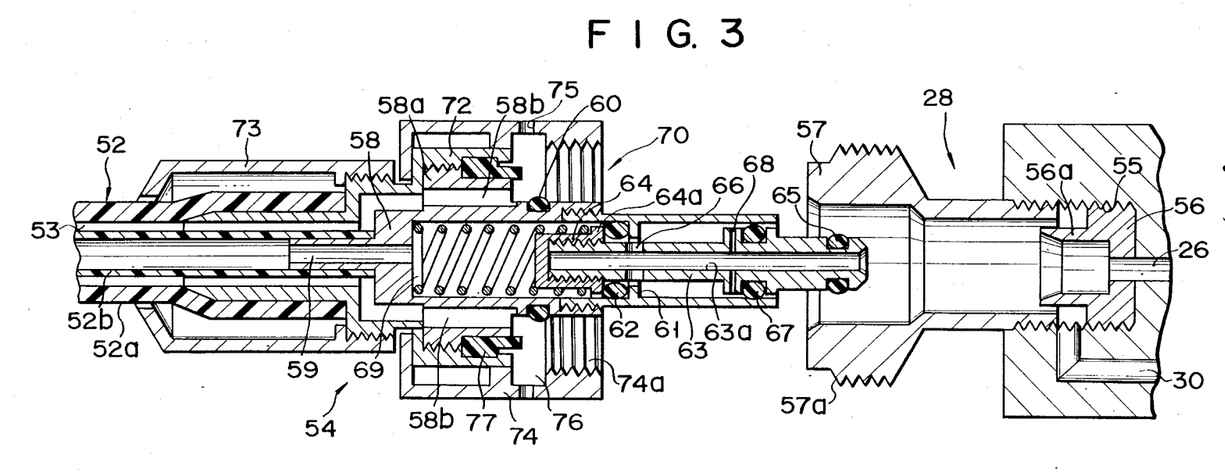
FIG. 3 is a sectional view showing a liquid feed plug and a liquid feed mouthpiece.

Liquid feed mouthpiece 28 and liquid feed plug 54 will now be described in detail.

As shown in FIG. 3, mouthpiece 28 includes blind hole 55 which is formed in connector 18. An internal thread is formed on the inner peripheral surface of hole 55. Abutting member 56 having cylindrical portion 56a is screwed in hole 55 so as to abut against the bottom of hole 55. The other end of liquid supply channel 26 opens to the inner bottom surface of portion 56a. Connecting cylinder 57 is screwed in blind hole 55, projecting outward from connector 18. Internal thread portion 57a is formed on the outer peripheral surface of the projected end portion of cylinder 57.

Liquid feed plug 54 has body 58 in the form of a bottomed cylinder. Radially projecting ring-shaped flange 58a is formed on the outer peripheral surface of body 58, located on the bottom side of body 58. Flange 58a is penetrated by a plurality of first which extend in the axial direction of body 58. From the bottom of body 58 protrudes coupling pipe 59 which communicates with the interior of body 58. The extreme end of pumping tube 52b is connected to pipe 59. 0-ring 60 is fitted on the outer peripheral surface of the middle portion of body 58. Ring-shaped rib 61 is formed on the inner peripheral surface of the middle portion of body 58. Also, ring-shaped seal member 62 is fixed to rib 61 and the inner peripheral surface of body 58, facing the bottom of body 58.

Figure 4:
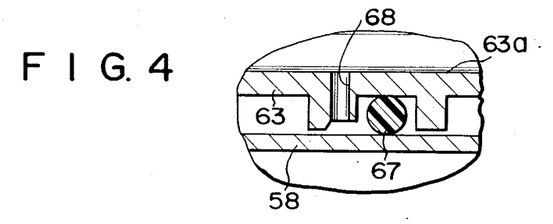
FIG. 4 is an enlarged sectional view showing part of the liquid feed plug.

Cylindrical piston 63 is slidably inserted in plug body 58. The rear end of piston 63 is closed by hat-shaped spring bearing 64, which has ring-shaped collar portion 64a projecting radially outward from piston 63. O-ring 65 is fitted on the front end portion of piston 63. Piston 63 is formed with a plurality of water holes 66 which, located adjacent to spring bearing 64, connect internal passage 63a of piston 63 with the outside. As shown in FIG. 4, O-ring 67 is held on the outer peripheral surface of piston 63, located between the front end of piston 63 and water holes 66. Ring 67 is in contact with the inner peripheral surface of body 58 in a liquid-tight manner. Further, piston 63 is formed with a plurality of lubricating water holes 68 which, adjoining ring 67, connect passage 63a of piston 63 with the outside. Coil spring 69 is disposed between the inner bottom surface of body 58 and collar portion 64a of spring bearing 64. Spring 69 urges piston 63 to project from body 58. When liquid feed plug 54 is disengaged from liquid feed mouthpiece 28, as shown in FIG. 3, collar portion 64a is pushed against seal member 62 by spring 69, and the front end portion of piston 63 is kept projecting from body 58. In this state, member 62 disconnects internal passage 63a of piston 63 from pumping tube 52b. If piston 63 is pushed into body 58 against the force of spring 69, collar portion 64a separates from member 62, so that passage 63a communicates with the interior of tube 52b. Thus, seal member 62 and piston 63 constitute switch valve mechanism 70.

Stepped cylindrical joint 72 is fitted on flange 58a of body 58, extending rearward from flange 58a. Outer tube 52a of liquid feed tube 52 is connected to the rear end of joint 72. Thus, air passage 53 of tube 52 communicates with first air holes 58b by means of a space defined between the outer surface of body 58 and the inner surface of joint 72. Cylindrical grip member 73, covering the connecting portion of liquid feed tube 52, is fixed to the rear end portion of joint 72. Also, cylindrical connecting ring 74 is rotatably mounted on joint 72 so as to be coaxial with body 58. External thread portion 74a, which is adapted to engage internal thread portion 57a of connecting cylinder 57, is formed on the inner peripheral surface of the front end portion of ring 74. A plurality of second air holes 75 are formed in the peripheral wall of ring 74, located between flange 58a of body 58 and thread portion 74a of ring 74. Air holes 75 connect with first air holes 58b by means of passage 76 defined in connecting ring 74. Ring-shaped second seal member 77 is fixed between flange 58a and joint 72. Seal member 77 engages the front end face of connecting cylinder 57 in an airtight manner when liquid feed plug 54 is connected to liquid feed mouthpiece 28.

The operation of the above-mentioned endoscope apparatus will now be described in detail.

In using the endoscope apparatus, connector 18 of endoscope 10 is first connected to air-liquid feed device 20. As a result, light source 42 is optically connected to light guide 24, while air pump 40 is connected to supply air supply channel 24 by air feed pipe 40a.

Then, connecting terminal 32 is connected to the video processing circuit (not shown). Also, connecting tube 50 of water tank 48 and liquid feed plug 54 are connected to connecting mouthpiece 44 of device 20 and liquid feed mouthpiece 28 of endoscope 10, respectively. When plug 54 is connected to mouthpiece 28, solenoid valve 46 is closed. Plug 54 is connected as follows.

Figure 5:
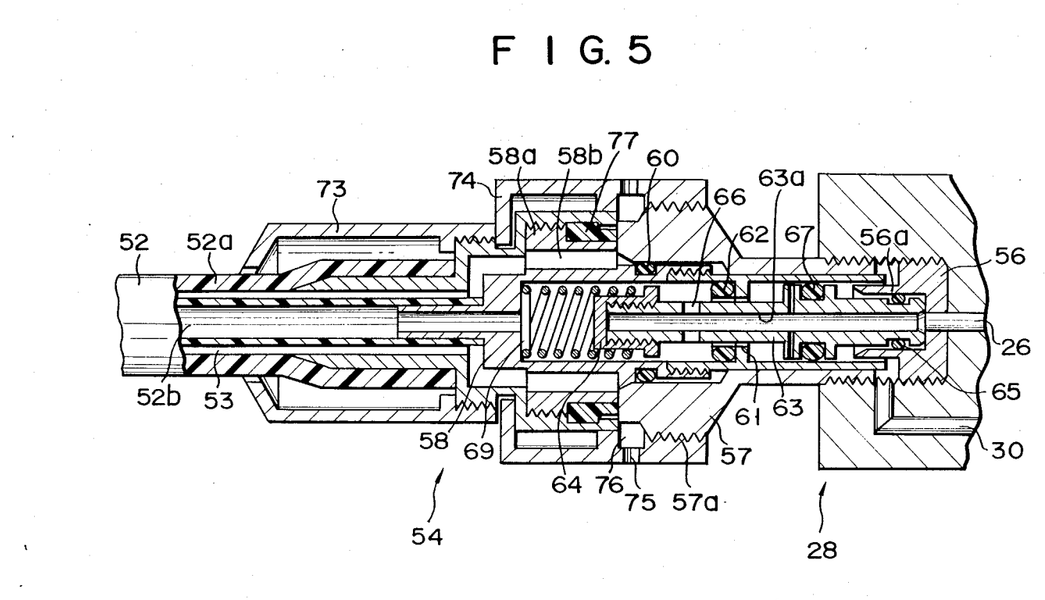
FIG. 5 is a sectional view showing the liquid feed plug and the liquid feed mouthpiece connected to each other.

First, plug body 58 and the front end portion of piston 63 are inserted into connecting cylinder 57 of liquid feed mouthpiece 28. Subsequently, external thread portion 74a of connecting ring 74 is screwed into internal thread portion 57a of cylinder 57. Thereupon, the front end of piston 63 is first inserted into cylindrical portion 56a of abutting member 56 to abut against the inner bottom surface of portion 56a. Then, piston 63 is forced into body 53, and collar portion 64a of spring bearing 64 is disengaged from first seal member 62. When connecting ring 74 is screwed fully into connecting cylinder 57, second seal member 77 is pressed against the end face of cylinder 57, as shown in FIG. 5. In this state, liquid supply channel 26 communicates with pumping tube 52b through internal passage 63a, water holes 66 of piston 63 and the interior of body 58. First air holes 58b are cut off from second air holes 75 by second seal member 77 and cylinder 57. O-rings 65 and 60 are in airtight contact with the inner peripheral surfaces of cylindrical portion 56a and cylinder 57, respectively. Thus, bypass passage 30 is closed air-tightly When the apparatus is connected to a power source (not shown), light source 42, air pump 40, and liquid pump 41 are actuated. A light beam emitted from light source 42 is transmitted through light guide 34 and radiated from illumination window 23. Air compressed by air pump 40 passes through air feed pipe 40a and upper-course portion 24a of air supply channel 24 to reach through hole 38a, and is released from leak hole 38b into the open air. Air compressed by liquid pump 41, on the other hand, flows through liquid feed pipe 41a and connecting tube 50 into tank 48, and pressurizes the water in tank 48. The compressed air further flows through air passage 53 in liquid feed tube 52 to first air holes 58b, where it is stopped. The compressed water in tank 48 flows into upper-course portion 26a of liquid supply channel 26 through pumping tube 52b, the inside space of body 58, water holes 66, and internal passage 63a of piston 63. At this time, the water is stopped by piston 38 of selector valve 36.

In this state, insertion section 14 of endoscope 10 is inserted into the body cavity of a patient. In supplying air through nozzle 22, the operator closes leak hole 38b of piston 38 with his or her finger. Thereupon, the compressed air, having so far been being released into the open air through hole 38b, comes to be injected into the body cavity through nozzle 22, passing through lower-course portion 24b of air supply channel 24.

In spraying a fluid mixture of air and water on view window 21 through nozzle 22 to wash window 21, the operator pushes piston 38 into the second position against the urging force of spring 39, while keeping leak hole 38b closed. As a result, upper- and lower-course portions 24a and 24b of air supply channel 24 are kept connected with each other by through hole 38a of piston 38, and upper- and lower-course portions 26a and 26b of liquid supply channel 26 are connected by annular groove 38c of piston 38. Accordingly, the compressed water in portion 26a of channel 26 flows through groove 38c into portion 26b. Thereafter, the water is mixed with the compressed air flowing through lower-course portion 24b of channel 24, and then sprayed on view window 21 through nozzle 22 for cleaning.

If air and liquid feed channels 24 and 26 are different in flow resistance, the optimum mixture ratio between air and water is set by regulating first and second throttle valves 43 and 45.

In removing liquid feed plug 54 from liquid feed mouthpiece 28 after the liquid feed operation, connecting ring 74 is first rotated to be loosened. When this is done, second seal member 77 is disengaged from the end face of connecting cylinder 57 to open passage 76. Thus, the compressed air in tank 48 is discharged into the open air via air passage 53, first air holes 58b, passage 76, and second air holes 75. As a result, tank 48 is released from pressure, so that water feed by compressed air is stopped. When ring 74 is not entirely removed from mouthpiece 28 yet, collar portion 64a of spring bearing 64 is not in contact with first seal member 62. Therefore, the compressed water remaining in upper-course portion 26a of liquid feed channel 26 flows through internal passage 63a of piston 63 and pumping tube 52 into tank 48. Thus, the water is prevented from running out of liquid feed plug 54.

When connecting ring 74 is entirely removed from liquid feed mouthpiece 28, spring 69 causes piston 63 to move until collar portion 64a abuts against seal member 62. As a result, pumping tube 52b is cut off from internal passage 63a of piston 63. Even if liquid feed plug 54 is turned upside down, therefore, the water in tank 48 will never leak. When liquid feed plug 54 is disengaged from mouthpiece 28, on the other hand, solenoid valve 46 of air-liquid supply device 20 is opened, so that the compressed air from liquid pump 41 is discharged into the open air through release pipe 41b. Thus, the compressed air cannot be delivered into tank 48, and leakage of water can be prevented more securely.

If the open end of connecting cylinder 54 of liquid feed mouthpiece 28 is closed by a cap (not shown), air supply channel 24 communicates with liquid supply channel 26 through bypass passage 30 and blind hole 55. In this state, therefore, the water in channel 26 can be drained off by introducing air into channel 26 by the agency of air pump 40.

Figure 6:
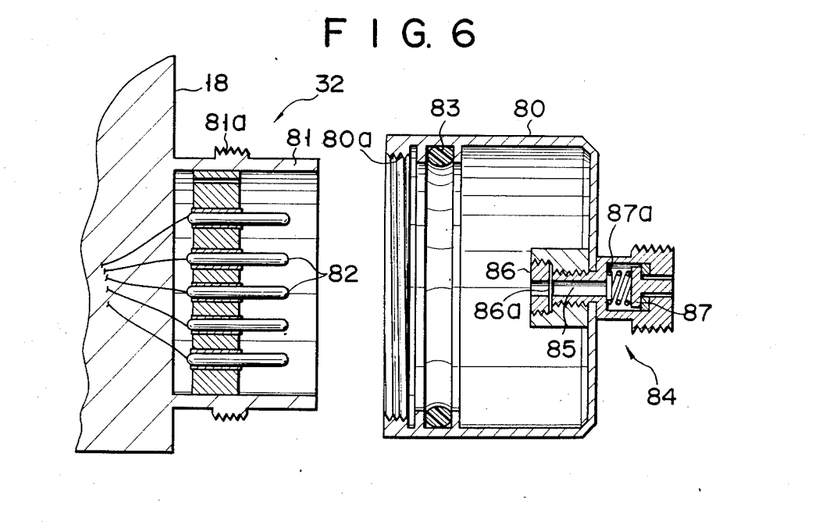
FIG. 6 is a sectional view showing a connecting terminal and a cap.

In cleaning or disinfecting endoscope 10, cap 80 is connected to connecting terminal 32 of connector 18. As shown in FIG. 6, terminal 32 includes connecting cylinder 81 protruding from connector 18 and a plurality of contact pins 82 arranged in cylinder 81. Thread portion 81a is formed on the outer peripheral surface of cylinder 81. Cap 80 is in the form of a bottomed cylinder having, on its inner peripheral surface, thread portion 80a adapted to engage thread portion 81a. Also, O-ring 83 is fixed to the inner peripheral surface of cap 80. Ring 83 is adapted to be in liquid-tight contact with the outer peripheral surface of cylinder 81. Ventilation mouthpiece 84 is attached to the bottom wall of cap 80. Mouthpiece 84 has through hole 85 which connect the inside and outside of cap 80. Goa sheet 86a is fixed inside the inner end of hole 85 by means of nut 86. Check valve 87 urged by spring 87a is disposed at the outer end of hole 85.

When cap 80 is mounted on connecting terminal 32, contact pins 82 are protected against corrosion due to medical fluids, and a liquid is prevented from flowing from terminal 32 into endoscope 10. Ventilation mouthpiece 84 permits necessary ventilation for the detection of leakage of water.

Figure 7:
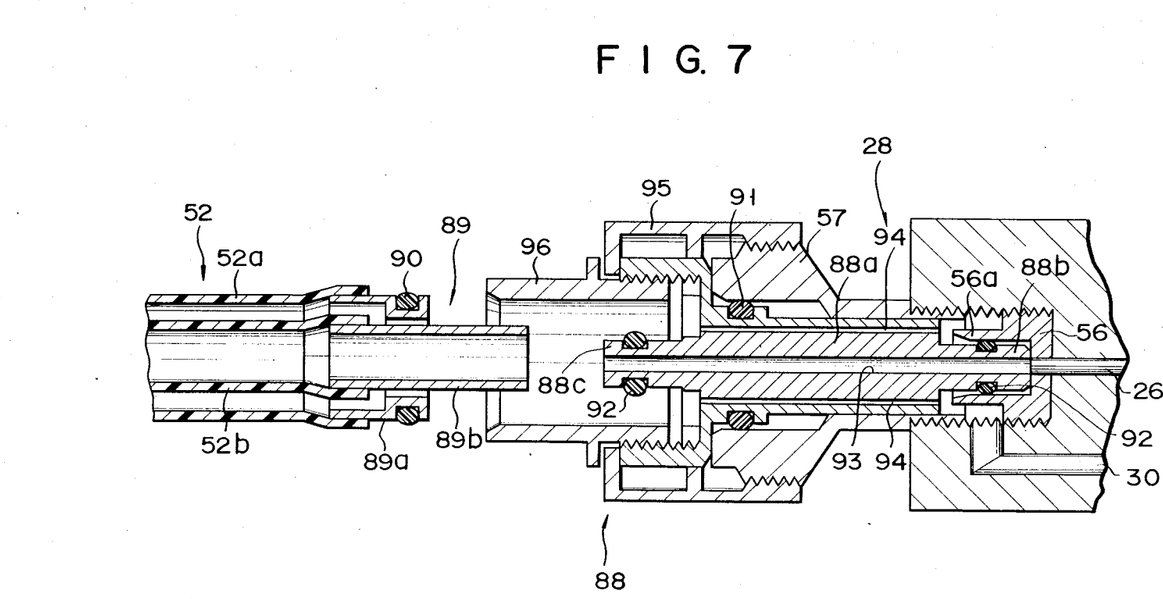
FIG. 7 is a sectional view of a liquid feed adapter.

To feed a liquid to endoscope 10 by means of air pump 40, liquid feed adapter 88 is attached to liquid feed mouthpiece 28, and double pipe 89 is mounted on the end of liquid feed tube 52 in place of liquid feed plug 54, as shown in FIG. 7. Pipe 89 includes outer pipe 89a and inner pipe 89b connected to outer tube 52a and pumping tube 52b; respectively. O-ring 90 is fitted on the outer peripheral surface of outer pipe 89a. Adapter 88 has cylindrical body 88a inserted in connecting cylinder 54 of liquid feed mouthpiece 28. O-ring 91 is fitted on the outer peripheral surface of body 88a, engaging the inner peripheral surface of cylinder 54 in a liquid-tight manner. Body 88a includes front-end projection 88b inserted in cylindrical portion 56a of abutting member 56, and rear-end projection 88c inserted in inner pipe 89b of double pipe 89. Two O-rings 92 are fitted on the outer peripheral surface of each of projections 88b and 88c.

Body 88a is formed with liquid passage 93 extending along the axis of body 88a and communicating with liquid supply channel 26, and a plurality of air passages 94 connecting with bypass passage 30. Connecting ring 95 engaging connecting cylinder 54 is rotatably mounted on the outer peripheral surface of body 88a. Also, body 88a is fixedly fitted with coaxial coupling ring 96. Outer pipe 89b is inserted in ring 96 in a liquid-tight manner.

When air pump 40 is actuated, compressed air is fed into tank 48 through bypass passage 30, air passage 94, the inside of outer pipe 89a, and air passage 53 of liquid feed tube 52. The water in tank 48 pressurized by the compressed air is delivered to liquid supply channel 26 via pumping tube 52b, inner piper 89b, and liquid passage 93.

According to the endoscope apparatus constructed in this manner, air-liquid supply device 20 is provided with separate pumps 40 and 41 for air and liquid feed. Even if the flow resistance of liquid supply channel 26 is increased from any causes, therefore, channel 26 can be fed with enough water, thus preventing excessive air supply. Further, selector valve 36 for controlling the air and water feed is provided at operating section 14 of endoscope 10. Therefore, the water compressed by liquid pump 41 is always on the point of entering valve 36, that is, upper-course portion 26a of liquid supply channel 26 is always filled with the compressed water. Accordingly, the moment valve 36 is activated, the fluid mixture of air and water is sprayed from nozzle 22. Thus, the endoscope apparatus of the invention is improved in spraying response.

The improved construction of liquid feed plug 54 can prevent water from leaking or running out even when plug 54 is removed from liquid feed mouthpiece 28 with the interior of water tank 48 being pressurized.

Figure 8:
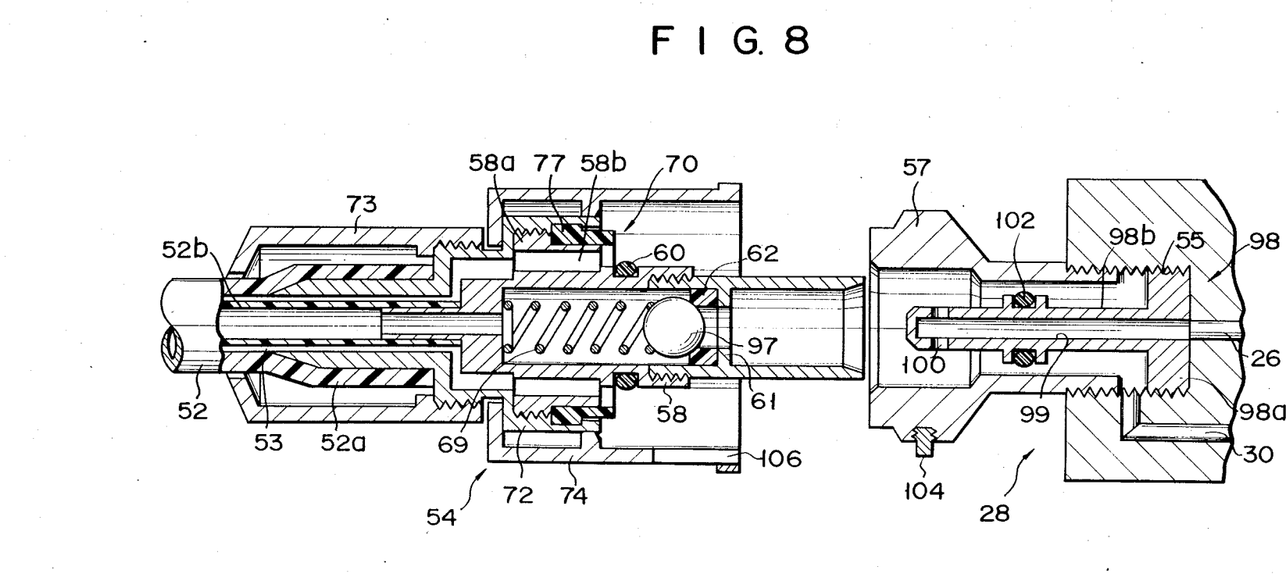
FIG. 8 is a sectional view showing the plug and a liquid feed mouthpiece.
Figures 9, 10:
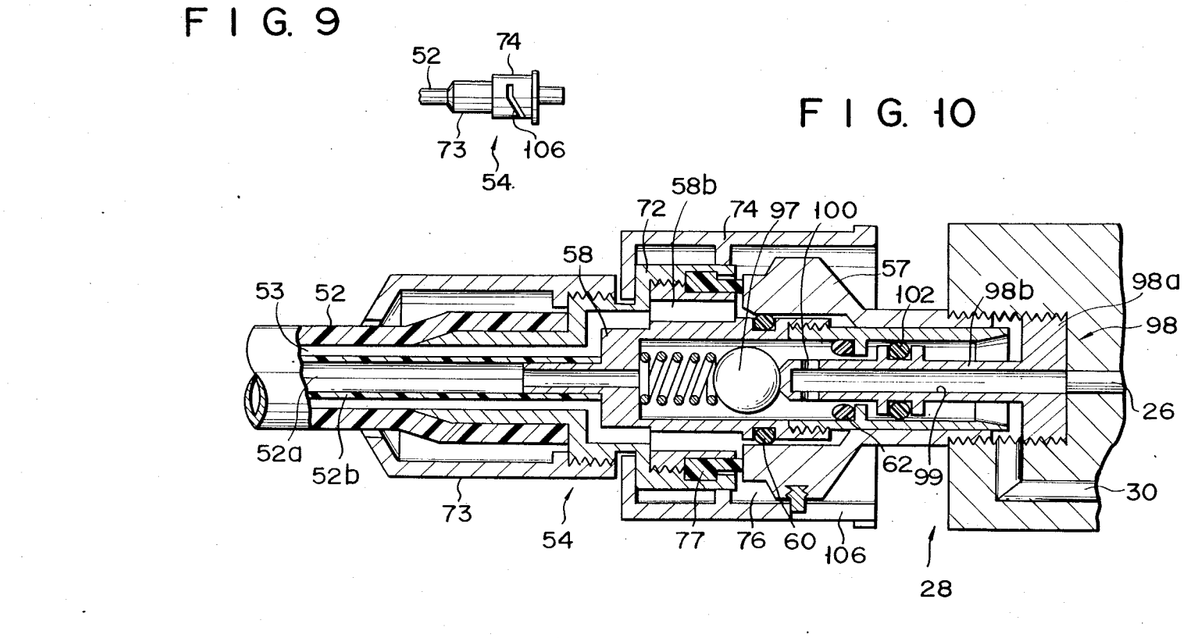
FIG. 9 is a side view of the plug.
FIG. 10 is a sectional view showing the plug and the mouthpiece connected to each other.

FIGS. 8, 9 and 10 show a modified example of liquid feed plug 54 and liquid feed mouthpiece 28. In the description to follow, the same reference numerals are used to designate like portions as used to denote the parts of the embodiment described above.

According to this modification, ball 97 is used in place of the piston. Ball 97 is disposed between the inner bottom surface of body 58 and first seal member 62, and is pressed against member 62 by spring 69. Liquid feed mouthpiece 28 includes pressure member 98 in place of the abutting member. Member 98 has base portion 98a screwed fully into blind hole 55, and pressure portion 98b extending from portion 98a to the region near the end opening of connecting cylinder 57. Water passage 99 is formed in portion 98b so as to communicate with liquid supply channel 26. Passage 99 extends to the distal end of portion 98b. Pressure portion 98b has, at its distal end portion, with a plurality of water holes 100 which connect passage 99 and the interior of cylinder 57. O-ring 102 is fitted on the outer peripheral surface of the middle portion of pressure portion 98b so as to engage the inner surface of plug body 58 in a liquid-tight manner. Pin 104 is fixed to the distal end portion of connecting cylinder 57, projecting outward in the radial direction of cylinder 57. As shown in FIG. 9, connecting ring 74 of plug 54 is formed with spiral groove 106 which engages pin 104. Groove 106 also serves as the second air holes of the above-mentioned embodiment.

When connecting ring 74 is coupled to connecting cylinder 57 of liquid feed mouthpiece 28, as shown in FIG. 10, pressure portion 98b penetrates first seal member 62 to press ball 97, thereby separating ball 97 from member 62. As a result, liquid supply channel 26 communicates with pumping tube 52a through water passage 99, water holes 100, and the inside of body 58.

The liquid feed plug according to this modification may provide the same effect and function of its counterpart in the above described embodiment.

What is claimed is:

1. An endoscope apparatus comprising:
   an endoscope including
   an operation section,
   an insertion section extending from the operation section,
   a universal cord extending from the operation section,
   a view window provided at the distal end of the insertion section,
   a washing nozzle provided at the distal end of the insertion section and adapted to spray a fluid mixture of air and water on the view window,
   a connector fixed to an extended end of the universal cord,
   an air supply channel and a liquid supply channel extending through the insertion section, operation section and universal section, and each having one end connected to the nozzle and the other end opening to the connector, and
   a selector mechanism provided at the operation section and shiftable between a first position where air and liquid passing through the air and liquid supply channels are prevented from flowing to the washing nozzle, and a second position where air and water are allowed to flow to the washing nozzle; and
   an air-liquid supply device connected to the connector, said device including
   an air pump connected to the other end of the air supply channel for supplying compressed air to the air supply channel,
   a tank connected to the other end of the liquid supply channel and stored with water, and
   a liquid pump for pressurizing the water in the tank to supply the water to the liquid supply channel.

2. The endoscope apparatus according to claim 1, wherein said selector mechanism includes a cylinder provided at the operation section to communicate with the air and liquid supply channels, a piston movable between the first and second positions in the cylinder, and an urging member for urging the piston toward the first position, said piston having a through hole adapted to open the air supply channel when the piston is located in either of the first and second positions, a leak hole communicating with the through hole and opening to the outside of the operating section, and a passage adapted to open the liquid supply channel when the piston is in the second position.

3. The endoscope apparatus according to claim 1, wherein said air-liquid supply device includes a first throttle valve disposed between the other end of the air supply channel and the air pump, for adjusting the flow resistance of the air supply channel, and a second throttle valve disposed between the tank and the liquid pump, for adjusting the flow resistance of the liquid supply channel.

4. The endoscope apparatus according to claim 1, wherein said connector includes a liquid feed mouthpiece communicating with the other end of the liquid supply channel, and said tank includes a tank body stored with water, a connecting tube for introducing the compressed air from the liquid pump into the tank, a liquid feed tube extending from the tank body and having therein an air passage opening into the tank and a water passage through which the water in the tank flows, and a liquid feed plug fixed to the extended end of the liquid feed tube and detachably connected to the liquid feed mouthpiece, said liquid feed plug having release means for releasing the compressed air from the tank body and the air passage into the open air when the liquid feed plug is removed from the liquid feed mouthpiece, and a valve mechanism for closing the liquid passage after the compressed air is released into the open air.

5. The endoscope apparatus according to claim 4, wherein said liquid feed plug includes a substantially cylindrical body having an inside space communicating with the liquid passage, and a release passage adapted to be closed by the liquid feed mouthpiece when the plug is connected to the mouthpiece and to connect the air passage with the open air when the plug is disengaged from the mouthpiece, and said valve mechanism includes a valve seat provided in the plug body, a valve member movable in the inside space of the plug body and cooperating with the valve seat, and an urging member disposed in the inside space of the plug body, for urging the valve member toward the valve seat.

6. The endoscope apparatus according to claim 5, wherein said valve member includes a piston having an internal passage for connecting the inside space of the plug body and the liquid supply channel when the liquid feed plug is connected to the liquid feed mouthpiece.

7. The endoscope apparatus according to claim 4, wherein said air-liquid supply device includes a release pipe connected, at one end, between the liquid pump and the tank and opening into the open air at the other end, and a solenoid valve attached to the release pipe and adapted to be opened when the liquid feed plug is removed from the liquid feed mouthpiece.

* * * * *